United States Patent

Ohta

[11] Patent Number: 5,311,444
[45] Date of Patent: May 10, 1994

[54] ABSORBANCE ANALYZER AND DATA PROCESSING METHOD FOR CHROMATOGRAPH

[75] Inventor: Hiroshi Ohta, Kadoma, Japan
[73] Assignee: Shimadzu Corporation, Kyoto, Japan
[21] Appl. No.: 906,972
[22] Filed: Jun. 30, 1992

[30] Foreign Application Priority Data

Jun. 30, 1991 [JP] Japan .................. 3-186792

[51] Int. Cl.$^5$ .................. G01N 21/72; G06K 9/46
[52] U.S. Cl. .................. 364/497; 364/498; 73/23.23; 73/23.36
[58] Field of Search .................. 364/496, 497, 498, 499, 364/500, 23.36; 73/61.52, 61.53, 61.69, 61.72, 23.23; 250/390.07, 341, 339, 304, 343, 576

[56] References Cited

U.S. PATENT DOCUMENTS

| | | |
|---|---|---|
| 3,797,300 | 3/1974 | Sato .................. 73/23.1 |
| 4,259,291 | 3/1981 | Smythe .................. 422/82 |
| 4,494,871 | 11/1981 | Futekov et al. .................. 356/315 |
| 4,546,643 | 10/1985 | Bonneyrat et al. .................. 73/61.52 |
| 4,618,769 | 10/1986 | Johnson et al. .................. 250/338 |
| 4,794,088 | 12/1988 | Miyaki et al. .................. 73/61.52 |
| 4,837,157 | 6/1989 | Turnell et al. .................. 73/61.52 |
| 4,843,243 | 6/1989 | Biemann et al. .................. 250/288 |
| 4,958,295 | 9/1990 | Davidson et al. .................. 364/497 |
| 4,990,250 | 2/1991 | Hellinger .................. 73/61.52 |
| 5,038,039 | 8/1991 | Wong et al. .................. 250/339 |
| 5,121,443 | 6/1992 | Tomlinson .................. 364/497 |
| 5,160,826 | 11/1992 | Cohen et al. .................. 250/339 |

FOREIGN PATENT DOCUMENTS

0351761  1/1990  European Pat. Off. .

OTHER PUBLICATIONS

European Search Report, Application Ser. No. 92106938.1, Sep. 17, 1992.

Primary Examiner—Thomas G. Black
Assistant Examiner—Tan Q. Nguyen
Attorney, Agent, or Firm—William L. Klima

[57] ABSTRACT

A measuring part measures the absorbance spectrum of an effluent fluid sample from a chromatograph in a constant cycle, and a base line calculating part calculates a base line including absorbance values on both ends of a designated wave number range with respect to every absorbance spectrum data as measured. A peak area calculating part calculates the peak area of the absorbance spectrum in the designated wave number range on the basis of the decided base line. A chromatogram is obtained by time change of the calculated peak area. Thus, it is possible to eliminate influences by other functional groups and fluctuation of the base line in an absorbance analyzer.

16 Claims, 5 Drawing Sheets

ABSORBANCE ANALYZER AND DATA PROCESSING METHOD FOR CHROMATOGRAPH

BACKGROUND OF THE INVENTION

1. Field of the Invention

The present invention relates to an absorbance analyzer which comprises an optical detector for measuring an absorbance spectrum in relation to a chromatograph such as a gas chromatograph or a liquid chromatograph. This absorbance analyzer can be employed for analyzing absorbance of an effluent fluid sample from a chromatograph, for measuring time change of a specific functional group or the like.

2. Description of the Background Art

A Fourier transform infrared spectrophotometer (FTIR) is adapted to analyze absorbance of an effluent gas from a gas chromatograph, in order to form a chromatograaph by time change of an absorption peak of a specific functional group. In this case, the absorbance value is integrated in a prescribed wave number range having absorption of the specific functional group, thereby recording its time change. Assuming that the wave number range is set as $v_1$ to $v_2$ and absorbance spectrum waveform at a time t is represented by A(t, $v$), the following value I' (t) is recorded:

$$I'(t) = \int_{v1}^{v2} A(t, v)dv$$

In general, a single organic substance has a plurality of functional groups every molecule, and absorbance spectra of such functional groups may be overlapped with each other in a certain wave number range. When a chromatogram is formed by wave number integration of absorbance in a conventional method, therefore, the as-formed chromatogram is not proportionate to only concentration of a single target functional group, but influenced by absorption of other functional groups in an adjacent wave number region, fluctuation of the base line of the absorbance spectrum, and the like. Thus, it is difficult to study the results of an analysis.

SUMMARY OF THE INVENTION

An object of the present invention is to provide an absorbance analyzer for obtaining time change of a specific functional group which is contained in a sample by removing influences by other functional groups and fluctuation of a base line.

FIG. 1 illustrates a mode of the present invention. A measuring part 2 is adapted to measure the absorbance spectrum of an effluent fluid sample from a chromatograph in a constant cycle, and a base line calculating part 4 decides a base line including absorbance values on both ends of a designated wave number range with respect to measurement data of every absorbance spectrum measured by the measuring part 2, while a peak area calculating part 6 calculates the peak area of the absorbance spectrum in the designated wave number range on the basis of the decided base line. A chromatogram is obtained by time change of the peak area which is calculated by the peak area calculating part 6.

FIG. 2 shows an exemplary operation of the present invention shown in FIG. 1.

Referring to FIG. 2, an area I(t) obtained by subtracting a region $I_2(t)$, which is enclosed by a trapezoid formed by connecting absorbance values of $v_1$ and $v_2$ by segments, from an integral value $I_1(t)$ of an absorbance spectrum A(t, $v$) in the designated wave number range $v_1$ to $v_2$ indicates the absorbance of the target region. This is expressed as follows:

$$I(t) = I_1(t) - I_2(t) \quad (1)$$
$$= \int_{v1}^{v2} A(t, v)dv - (v_2 - v_1)\{A(t, v_1) + A(t, v_2)\}/2$$

where $v$ represents the wave number in the absorbance measurement, and A(t, $v$) represents the absorbance spectrum of the sample changing over time, with the integration range of $v_1$ to $v_2$ ($v_1 < v_2$). The integral value $I_1(t)$ obtained in the designated wave number range $v_1$ to $v_2$ includes a fluctuation component of the base line in this wave number range, due to the absorbance spectrum of an adjacent functional group, a fluctuation factor appearing on the spectrum, and the like. A stable chromatogram can be obtained by subtracting the area $I_2(t)$ of the base line portion from $I_1(t)$.

FIG. 3 shows another mode of the present invention. Referring to FIG. 3, an absorbance spectrum is secondarily differentiated in place of calculating a base line. A secondary differential operating part 5 secondarily differentiates each absorbance spectrum data measured by a measuring part 2 in a designated wave number range, while a peak area calculating part 6a calculates the area of a region between the secondary differential function obtained in the secondary differential operating part 5 and wave number coordinate in the designated wave number range. Time change of the peak area calculated by the peak area calculating part 6a forms a chromatogram.

According to the present invention, the peak area of an absorbance spectrum is calculated on the basis of a base line including absorbance values on both ends of a designated wave number range of the absorbance spectrum, or the peak area is calculated with respect to a secondary differential function of the absorbance spectrum, to thereafter obtain a chromatogram, whereby it is possible to obtain a chromatogram while effectively eliminating influences by absorption peaks of other functional groups appearing in close wave number range and fluctuation of the base line. Thus, it is possible to more precisely identify a component separated in a chromatograph such as a gas chromatograph.

The foregoing and other objects, features, aspects and advantages of the present invention will become more apparent from the following detailed description of the present invention when taken in conjunction with the accompanying drawings.

DESCRIPTION OF THE PREFERRED EMBODIMENT

Figure 4:
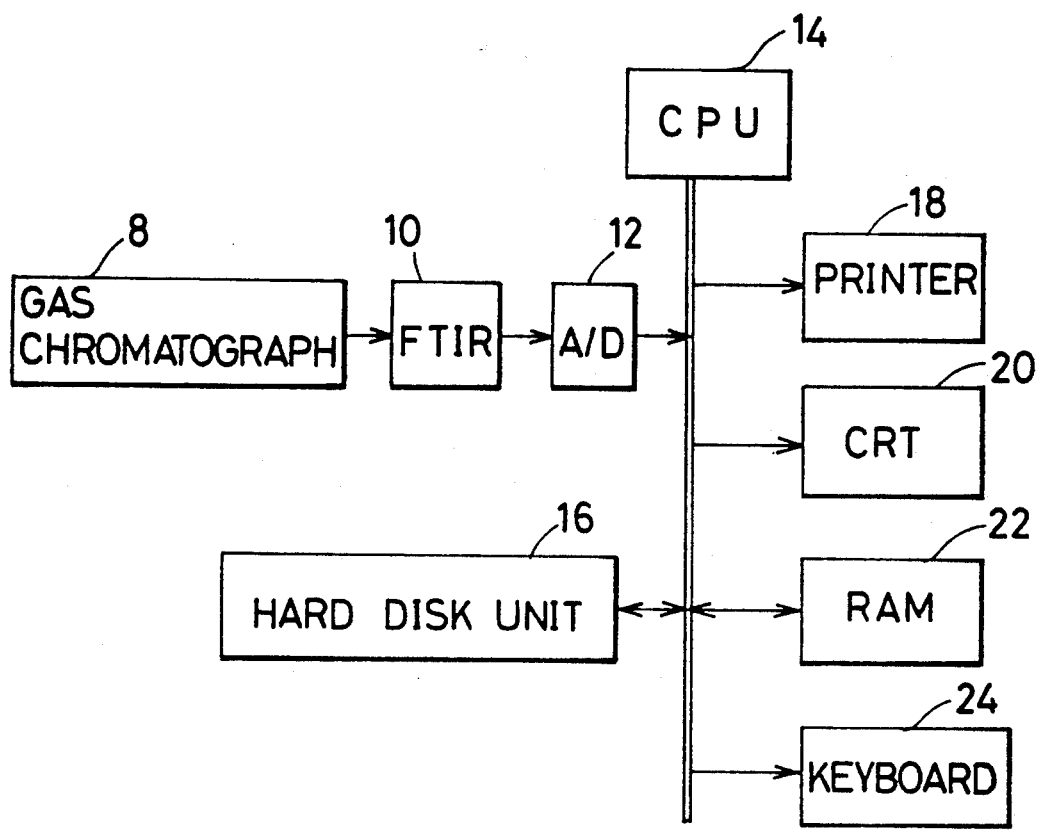
FIG. 4 is a block diagram showing an embodiment of the present invention.

FIG. 4 illustrates an apparatus which is employed in an embodiment of the present invention.

An effluent gas from a gas chromatograph 8 is guided to a sample cell, so that its infrared absorption spectrum is measured by an FTIR 10. An interferogram (interference waveform) measured by the FTIR 10 is converted to a digital signal through an A-D converter 12, and incorporated in a CPU 14. The CPU 14 is connected with a hard disk unit 16 which stores the absorbance spectrum data, a printer 18 which records the result of calculation, a CRT 20, a RAM 22 which stores the result of calculation of a peak area, a keyboard 24 for carrying out the operation, and the like.

Figure 1:
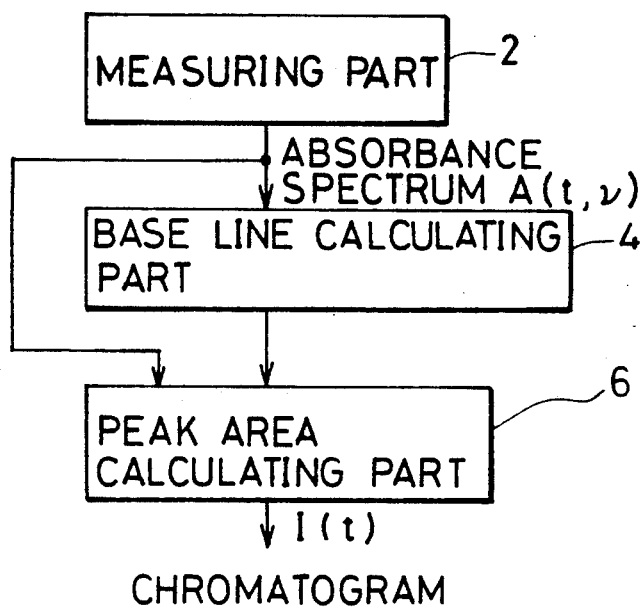
FIG. 1 is a block diagram showing a mode of the present invention.
Figure 2:
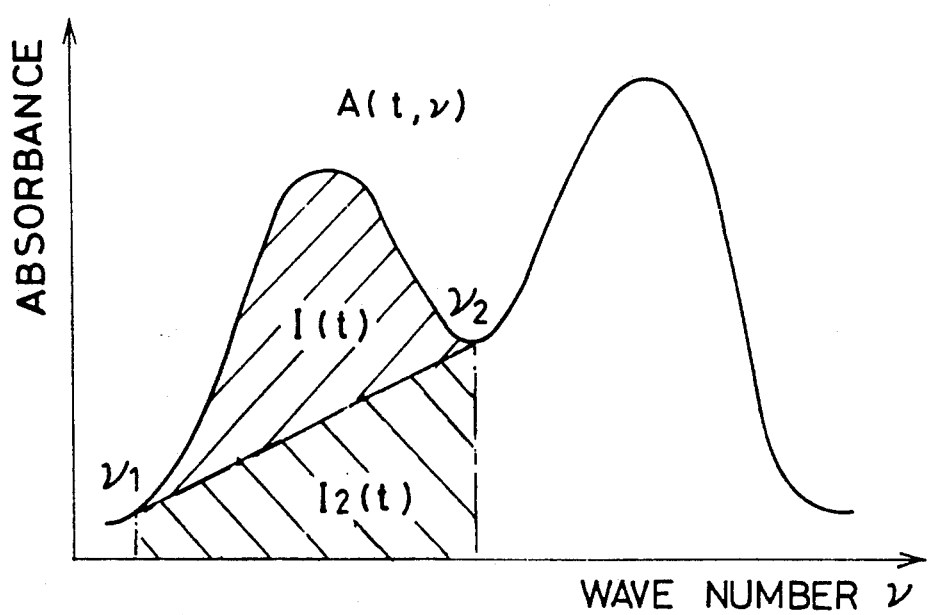
FIG. 2 is an absorbance spectrum diagram showing an exemplary operation of the present invention shown in FIG. 1.
Figure 3:
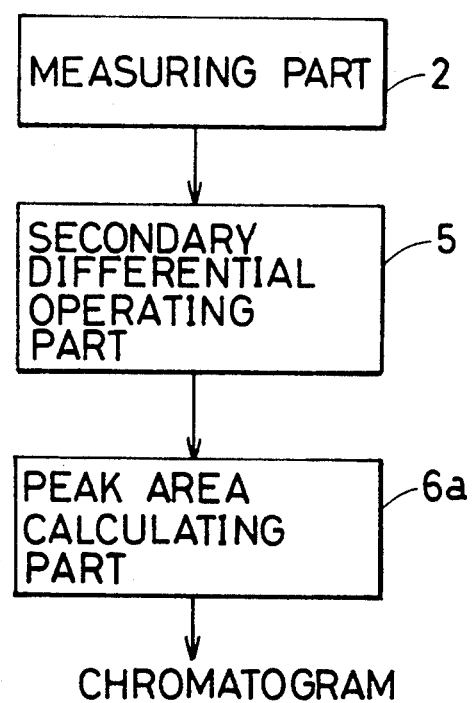
FIG. 3 is a block diagram showing another mode of the present invention.

As to relations between FIGS. 1 and 2 and FIG. 4, the measuring part 2 corresponds to the gas chromatograph 8 and the FTIR 10, while the base line calculating part 4, the peak area calculating part 6, the secondary differential operating part 5 and the peak area calculating part 6a are implemented by the CPU 14, the hard disk unit 16 and the RAM 22.

In an operation for storing the absorbance spectrum of the effluent gas from the gas chromatograph 8 in the hard disk unit 16, the FTIR 10 introduces the effluent gas from the gas chromatograph 8 into a measuring cell and operates in a constant cycle so that data of the interferogram per operation is incorporated in the CPU 14 through the A-D converter 12. The CPU 14 Fourier-transforms the interferogram data to absorbance spectrum data, and stores the same in the hard disk unit 16.

After completion of the measurement, the CPU 14 processes the stored data to calculate data of a chromatogram and displays the same on the CRT 20, or outputs the same to the printer 18 for drawing the chromatogram.

Figure 5:
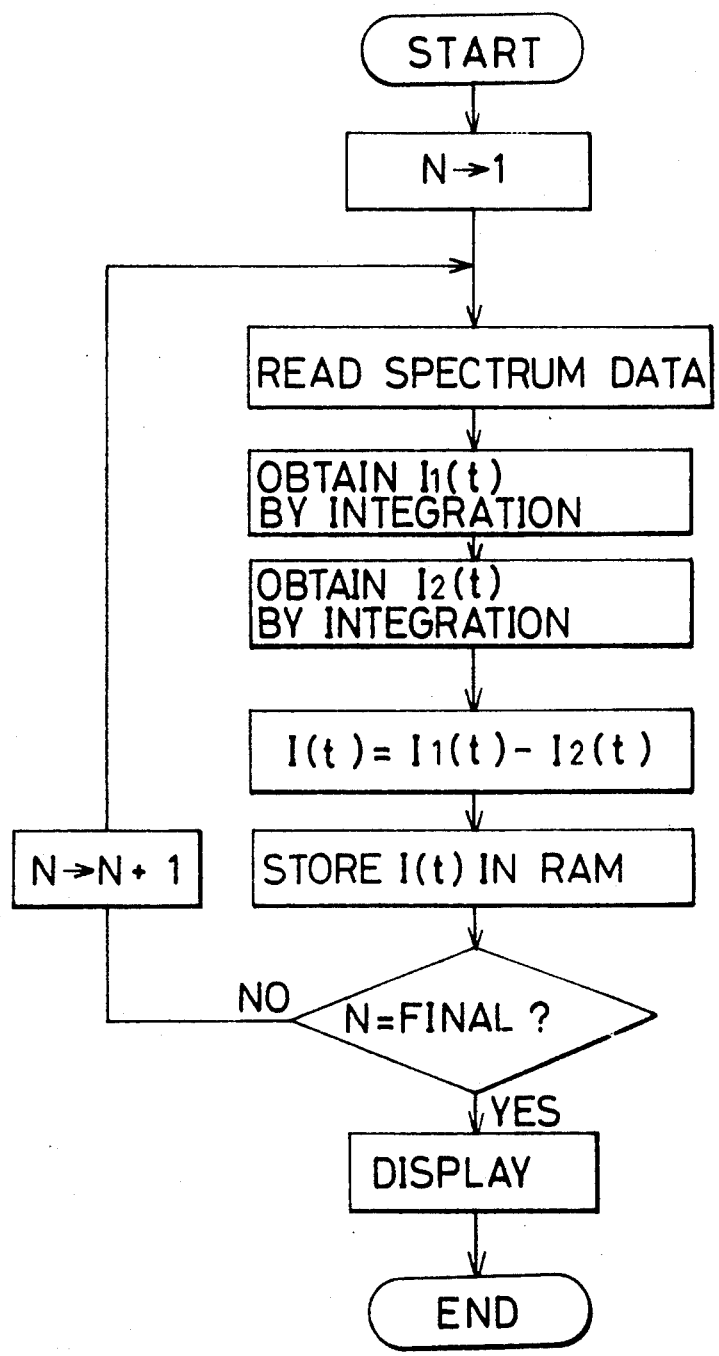
FIG. 5 is a flow chart showing an exemplary operation of the present invention.

With reference to a flow chart shown in FIG. 5, a data processing operation of the CPU 14 is now described.

First, an operator designates a single spectrum region ($v_1$ to $v_2$) through the keyboard 24, to start the data processing operation. The hard disk unit 16 stores absorbance spectrum data with data numbers N, which are allocated every operation of the FTIR 10 to indicate the order of the data. The absorbance spectrum data stored in the hard disk unit 16 are identified by the numbers N, such that absorbance spectrum data which are different by one number from each other are those of effluent gases flowing out from the gas chromatograph at times which are different by one operation cycle of the FTIR 10 from each other. The data numbers N are started from 1, so that absorbance spectrum data $A(N, v)$ of a designated number is read out from the hard disk unit 16 to be subjected to integration of $I_1(t)$ in the above expression (1). Then, a base line portion $I_2(t)$ of a designated peak region is integrated and subtracted from $I_1(t)$, thereby calculating the area of a substantial peak portion $I(t)$.

The result of such calculation is stored in the RAM 22, which in turn determines whether or not the current data number N is the final value. If the current data number N is not the final value, 1 is added to N and the same operation is repeated as to data of the next order number. Thus, data of the chromatogram $I(t)$ are stored in the RAM 22, and the data processing operation is terminated when the current data number N reaches the final value. Thereafter the data of $I(t)$ are read out from the RAM 22 to be displayed on the CRT 20 or recorded in the printer 18, to form a chromatogram.

In the aforementioned embodiment, absorbance spectrum are temporarily incorporated in the hard disk unit 16 every time before completion of each analysis by a chromatograph to be then data-processed.

Alternatively, such a data processing operation may be carried out every absorbance spectrum measuring operation which is repeated every operation cycle of the FTIR 10, to record a chromatogram in real time.

As to the method of deciding the base line, approximation is made by the straight line which connects the absorbance values on both ends of the designated wave number range in FIG. 2. Alternatively, the base line may be decided by a spline function through absorbance data in several points around the designated wave number range. In this case, it is possible to more precisely correct the base line.

It is also possible to reduce fluctuation of an absorbance integral value caused by noise or fluctuation of a base line by secondarily differentiating an absorbance spectrum in a designated wave number range. A method employing such secondary differential processing is now described.

Figure 6:
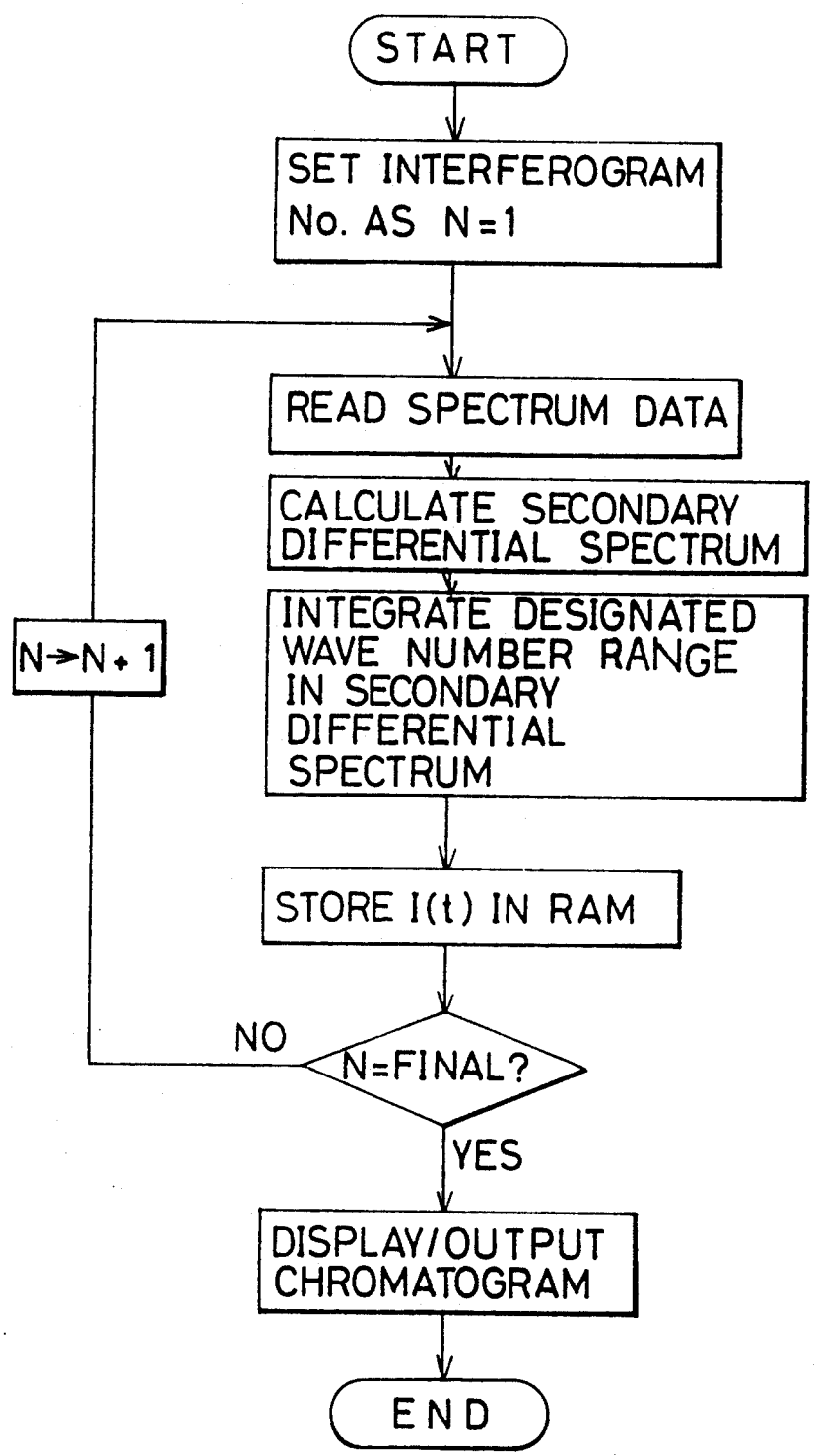
FIG. 6 is a flow chart showing an operation for carrying out secondary differentiation.

FIG. 6 illustrates an operation for secondary differential data processing made by a CPU. When an operator designates a single spectrum region $v_1$ to $v_2$ through a keyboard to start the data processing operation, data having a data number N of 1 is read out from a hard disk unit, so that a designated peak region is secondarily differentiated. Integration of the as-obtained secondary differential spectrum in the designated wave number range is carried out, so that the as-obtained integral value $I(t)$ is stored in a RAM to form a chromatogram file. The same processing is repeated until the data number reaches the final value, and the series of data $I(t)$ are read out from the RAM after completion of the data processing operation to be displayed on a CRT in the form of a chromatogram, or recorded in a printer.

Also in the case of secondary differentiation, a data processing operation including secondary differentiation and area integration may be carried out every absorbance spectrum measuring operation which is repeated in a constant cycle to record a chromatogram in real time, in place of the data processing operation carried out after temporarily incorporating the series of data in the hard disk unit as shown in FIG. 6.

When such secondary differentiation is carried out, it is possible to remove a direct current component and inclination of the base line of the absorbance spectrum.

The absorbance analyzer according to the present invention is also applicable to a liquid chromatograph, a supercritical chromatograph, a thin layer chromatograph and the like, in addition to the gas chromatograph.

Although the present invention has been described and illustrated in detail, it is clearly understood that the same is by way of illustration and example only and is not to be taken by way of limitation, the spirit and scope of the present invention being limited only by the terms of the appended claims.

The features disclosed in the foregoing description, in the claims and/or in the accompanying drawings may, both, separately and in any combination thereof, be material for realising the invention in diverse forms thereof.

What is claimed is:

1. An absorbance analyzer for obtaining a chromatograph from a series of absorbance spectra, comprising:
   a measuring part for measuring the absorbance spectra dispersed over a wave number range as components in an effluent fluid sample from a chromatograph in a constant cycle;
   a base line calculating part for deciding a base line including absorbance values on both ends of a designated wave number range with respect to each absorbance spectrum data measured by said measuring part; and
   a peak area calculating part for calculating the peak area of the absorbance spectra in said wave number range on the basis of decided said base line,
   thereby obtaining the chromatogram by time change of said peak area calculated by said peak area calculating part.

2. An absorbance analyzer in accordance with claim 1, wherein
   said base line calculating part regards a straight line connecting said absorbance values on both ends of said designated wave number range as a base line, and
   said peak area calculating part calculates said peak area by subtracting the area of a region between said straight line being obtained as said base line in said designated wave number range and a wave number coordinate from the area of a region between the absorbance spectrum and the wave number coordinate in said designated wave number range.

3. An absorbance analyzer in accordance with claim 1, wherein
   said base line calculating part obtains a spline function through absorbance data of several points around said designated wave number range to regard the result as said base line, and
   said peak area calculating part calculates said peak area by subtracting the area of a region between said spline function being obtained as said base line in said designated wave number range and a wave number coordinate from the area of a region between the absorbance spectrum and the wave number coordinate in said designated wave number range.

4. An absorbance analyzer in accordance with claim 1, wherein said absorbance spectrum obtained by said measuring part is temporarily stored in a storage unit, and thereafter said base line calculating part and said peak area calculating part perform operations on the basis of data called from said storage unit.

5. An absorbance analyzer in accordance with claim 4, wherein absorption spectrum data are atored in said storage unit with data numbers corresponding to data sampling order in said measuring part.

6. An absorbance analyzer in accordance with claim 1, wherein the absorbance spectrum obtained in said measuring part is subjected to operations by said base line calculating part and said peak area calculating part every measuring operation.

7. An absorbance analyzer in accordance with claim 1, wherein said chromatograph is a gas chromatograph, and said measuring part is a Fourier transform infrared spectrophotometer.

8. An absorbance analyzer for obtaining a chromatograph from a series of absorbance spectra, comprising:
   a measuring part for measuring the absorbance spectra dispersed over a wave number range as components in an effluent fluid sample from a chromatograph in a constant cycle;
   a secondary differential operating part for secondarily differentiating each absorbance spectrum data measured by said measuring part in a designated wave number range; and
   a peak area calculating part for calculating the area of a region between a secondary differential function obtained in the above in said designated wave number range and a wave number coordinate,
   thereby obtaining the chromatogram by time change of a peak area calculated by said peak area calculating part.

9. An absorbance analyzer in accordance with claim 8, wherein the absorbance spectrum obtained by said measuring part is temporarily stored in a storage unit and thereafter said secondary differential operating part and said peak area calculating part perform operations on the basis of data called from said storage unit.

10. An absorbance analyzer in accordance with claim 9, wherein absorption spectrum data are stored in said storage unit with data numbers corresponding to data sampling order in said measuring part.

11. An absorbance analyzer in accordance with claim 8, wherein the absorbance spectrum obtained in said measuring part is subjected to operations by said base line calculating part and said peak area calculating part every measuring operation.

12. An absorbance analyzer in accordance with claim 8, wherein said chromatograph is a gas chromatograph, and said measuring part is a Fourier transform infrared spectrophotometer.

13. A data processing method comprising the steps of:
   measuring the absorbance spectrum of an effluent fluid sample from a chromatograph in a constant cycle;
   designating a wave number range with respect to data of measured said absorbance spectrum;
   deciding a base line to include absorbance values on both ends of designated said wave number range;
   calculating the peak area of the absorbance spectrum in said designated wave number range on the basis of decided said base line; and
   obtaining a chromatogram by time change of said peak area.

14. A data processing method in accordance with claim 13, wherein said base line is a straight line connecting said absorbance values on both ends of said designated wave number range.

15. A data processing method in accordance with claim 13, wherein said base line is a spline function obtained from absorbance data of several points around said designated wave number range.

16. A data processing method comprising the steps of:
   measuring the absorbance spectrum of an effluent fluid sample from a chromatograph;
   secondarily differentiating each absorbance spectrum data while designating a wave number range;
   calculating the peak area of a region between a secondary differential function and a wave number coordinate in designated said wave number range; and
   obtaining a chromatogram by time change of said peak area.

* * * * *